United States Patent
Lerch et al.

[11] 3,959,261
[45] May 25, 1976

[54] BIPHENYL COMPOUNDS

[75] Inventors: Ansgar Lerch, Kirrlach; Alfred Popelak, Rimbach; Kurt Stach, Mannheim; Klaus Hardebeck, Ludwigshafen (Rhine); Wolfgang Schaumann, Heidelberg, all of Germany

[73] Assignee: Boehringer Mannheim GmbH, Mannheim-Waldhof, Germany

[22] Filed: June 25, 1974

[21] Appl. No.: 482,956

[30] Foreign Application Priority Data
July 10, 1973 Germany............................ 2334973

[52] U.S. Cl.................. 260/239.6; 260/239.65; 260/397.7 R
[51] Int. Cl.$^2$............. C07D 237/00; C07D 239/00; C07D 241/00; C07D 251/00
[58] Field of Search.......... 260/239.6, 239.65, 397.7

[56] References Cited
UNITED STATES PATENTS

| | | | |
|---|---|---|---|
| 3,816,482 | 6/1974 | Felt et al....................... | 260/397.7 R |
| 3,843,662 | 10/1974 | Holland....................... | 260/397.7 R |
| 3,860,582 | 1/1975 | Schoenberg et al......... | 260/397.7 R |

OTHER PUBLICATIONS

Chem. Abst. 73 76889(z) (1970) – Feit et al. "Sulfamoylbenzoic Acid Derivatives".

J. Med. Chem. 14(5) pp. 432–439 (1971) – Feit – "Aminobenzoic Acid Diuretics".

*Primary Examiner*—Sam Rosen
*Assistant Examiner*—D. W. Robinson
*Attorney, Agent, or Firm*—Burgess, Dinklage & Sprung

[57] ABSTRACT

Novel biphenyl derivatives of the formula:

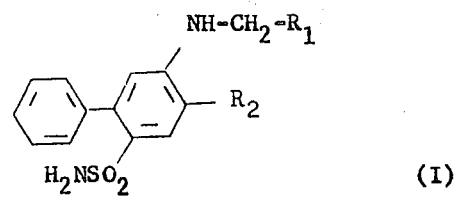

wherein
$R_1$ is phenyl, furyl or thienyl; and
$R_2$ is carboxyl or tetrazolyl-(5);

and the pharmacologically compatible salts thereof display outstanding diuretic and saluretic properties.

7 Claims, No Drawings

BIPHENYL COMPOUNDS

The present invention is concerned with new biphenyl compounds and with therapeutic compositions containing them.

The new biphenyl derivatives according to the present invention are compounds of the formula:

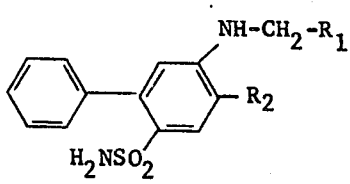

(I)

wherein
$R_1$ is phenyl, furyl and thienyl; and
$R_2$ is carboxyl or tetrazolyl-(5);
and the pharmacologically compatible salts thereof.

We have found that the new compounds of formula (I) are characterized by outstanding diuretic and saluretic properties.

The new compounds of formula (I) according to the present invention can be prepared, for example, by one of the following methods:

a. reaction of a compound of the formula:

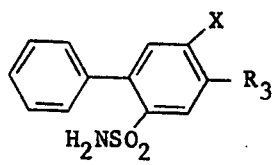

(II)

wherein $R_3$ has the same meaning as $R_2$ above or is a group which can be converted into $R_2$ and X is a reactive residue, with an amine of the formula:

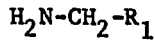

(III)

wherein $R_1$ has the same meaning as above; or b. reaction of a compound of the formula:

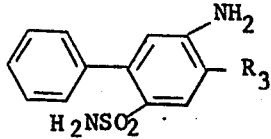

(IV)

wherein $R_3$ has the same meaning as above, with a compound of the formula:

(V), wherein $R_1$ has the same meaning as above and Z is a reactive ester group, or with a compound of the formula:

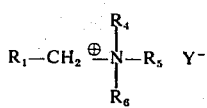

(VI), wherein $R_1$ has the same meaning as above and $R_4$, $R_5$ and $R_6$, which can be the same or different, are lower alkyl radicals and $Y^-$ is an acid anion, or with a compound of the formula:

$$OHC-R_1 \quad (VII),$$

wherein $R_1$ has the same meaning as above, and simultaneous or subsequent hydrogenation, and when $R_3$ is a radical which can be converted into a carboxyl group or into a tetrazolyl-(5) radical, this is then converted into $R_2$, whereafter, if desired, the compound obtained is converted into a pharmacologically compatible salt.

The reactive residue X in compounds of formula (II) can be, for example, a halogen atom, a nitro group or an arylsulfonyloxy radical, preferably a p-toluene-sulfonyloxy radical.

Residues which can be converted into a carboxyl group are preferably esterified carboxyl groups, carboxamido and nitrile groups, as well as a carboxyl group in the form of a salt with an inorganic or organic base. Groups which can be converted into a tetrazolyl-(5) radical are preferably nitrile, thioamido, imido ester and amidine groups.

Compounds of formula (V) with a reactive ester group Z include, for example, halides, the quaternary ammonium compounds thereof, for example with pyridine, and sulfonic acid ester groups which can easily be split off, for example tosylate and brosylate radicals.

The alkyl radicals $R_4$, $R_5$ and $R_6$ can contain up to 3 carbon atoms, methyl being preferred.

The acid anion $Y^-$ can be, for example, a halide or hydrogen sulfate ion.

The process according to the present invention is carried out at a temperature between 60° and 180°C, preferably with the use of an excess of the basic reaction component. If the reaction results in the formation of an acid, then the excess of basic reaction component simultaneously serves to take up this acid. However, for this purpose, there can also be used other inorganic or organic bases or basically-reacting compounds; as examples, there may be mentioned alkali metal carbonates, calcium oxide, triethylamine, dimethylaniline and pyridine. The reaction can be carried out with or without the use of an inert solvent or diluent. If, however, a solvent of diluent is used, then this is preferably an aromatic hydrocarbon, ethyleneglycol, ethyleneglycol monomethyl ether, diethyleneglycol dimethyl ether, dimethyl formamide or dimethyl sulfoxide. When carrying out reactions with the use of inexpensive halides of formula (V), then these can themselves be used as solvents for the reaction.

The reaction of the primary amines of formula (IV) with carbonyl compounds of formula (VII) is advantageously carried out with the use of an excess of the carbonyl compound and with the addition of an acid, for example, glacial acetic acid or p-toluene-sulfonic acid, at 0° – 40°C. In this case, a Schiff base is first formed which is subsequently reduced either catalytically or with the use of a reduction agent, for example sodium borohydride, in an inert solvent.

When $R_3$ is an esterified carboxyl group or a carboxamido or nitrile group, it is subsequently converted into a carboxyl group by hydrolysis, preferably in an alkaline medium.

When it is desired to obtain compounds of formula (I) in which $R_2$ is a tetrazolyl-(5) radical, then the corresponding compounds in which $R_3$ is a nitrile, thioamido, imido ester or amidine group are subsequently reacted with a hydrazoic acid or, preferably, with a salt thereof, the reaction being carried out in an inert solvent, preferably in dimethyl formamide.

If desired, the products obtained can be reacted with organic or inorganic bases to give the corresponding salts. As physiologically compatible salts, there may be mentioned, in particular, the alkali metal, alkaline earth metal and ammonium salts, which can be prepared, for example, by reaction with an aqueous solution of sodium hydroxide, potassium hydroxide or ammonia or of the corresponding carbonates.

The starting materials of formula (II) are new compounds. They can be obtained, for example, from compounds of the formula:

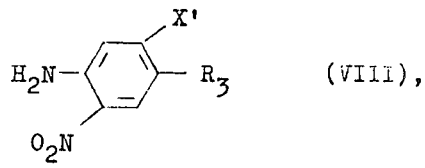

wherein $R_3$ has the same meaning as above and $X'$ is the same as X or is a hydroxyl group, by diazotizing in the presence of benzene to introduce the second phenyl ring, subsequently reducing the nitro group, preferably by catalytic hydrogenation, or, if $R_3$ is a nitrile group, with iron in ammonium chloride solution or with stannous chloride in hydrochloric acid, or when $X'$ is a nitro group, by selective reduction with hydrogen sulfide or an alkali metal salt thereof, whereafter the amino group thus formed is diazotized and, by reaction with sulfur dioxide in the presence of a copper salt, converted into the corresponding sulfochloride which is reacted with ammonia to give the desired sulfonamide.

In the preparation of the starting compounds of formula (II), the radical $R_3$ can be changed after any desired step. For example, a carboxylic acid can be esterified in known manner, an ester can be saponified or a carboxamide can be converted into a nitrile and this, in turn, converted into a tetrazole compound. If $X'$ is a hydroxyl group, then this can be converted, at any desired step, into, for example, a tosyloxy group.

The starting compounds of formula (IV) are also new compounds. They can be obtained by the reaction of compounds of formula (II) with ammonia, preferably with the use of a lower alcohol as solvent, or, if X is a nitro group, also by reduction or by catalytic hydrogenation.

The compounds of formulae (II) and (IV), which are valuable intermediates in the above-described process according to the present invention, are also the subject of the present invention.

The following Examples illustrate the invention:

EXAMPLE 1

Preparation of
3-Furfurylamino-6-sulfamoyl-biphenyl-4-carboxylic acid 35 g. 3-chloro-6-sulfamoyl-biphenyl-4-carboxylic acid were heated for 10 hours at 150°C. with 200 ml. furfurylamine. After cooling the reaction mixture, 1N aqueous sodium hydroxide solution was added thereto, followed by extraction with methylene chloride. The aqueous phase was treated with active charcoal, filtered and the filtrate acidified with 2N hydrochloric acid. The crude product which precipitated out was filtered off with suction and recrystallized from ethanol. There was obtained 15 g. (36% of theory) 3-furfurylamino-6-sulfamoyl-biphenyl-4-carboxylic acid, which decomposed at 206° – 208°C.

The 3-chloro-6-sulfamoyl-biphenyl-4-carboxylic acid used as starting material was prepared in the following manner:

175 g. 4-amino-2-chloro-5-nitrobenzoic acid were suspended in 1.8 liters ethanol, 350 ml. concentrated sulfuric acid was added dropwise thereto, while stirring, and the reaction mixture was boiled under reflux for 4 hours. After cooling, the reaction mixture was left to stand for 1 hour in the cold and the precipitated ester then filtered off with suction. The ethyl 4-amino-2-chloro-5-nitrobenzoate thus obtained melted at 172° – 173°C.

100 g. ethyl 4-amino-2-chloro-5-nitrobenzoate were suspended in a mixture of 500 ml. benzene and 250 ml. glacial acetic acid and a solution of 50 g. n-butyl nitrite in 200 ml. benzene slowly added thereto dropwise, while stirring, the temperature thereby not being allowed to increase above 30°C. The reaction mixture was then stirred for 1 hour and the benzene solution shaken out first with water, then with an aqueous solution of sodium bicarbonate and thereafter again with water. The benzene was distilled off in a vacuum and the residue recrystallized from methanol, with the addition of active charcoal. There was obtained 59 g. ethyl 3-chloro-6-nitro-biphenyl-4-carboxylate which melted at 65° – 67°C.

100 g. ethyl 3-chloro-6-nitrobiphenyl-4-carboxylate were boiled with 400 ml. ethanol and 400 ml. 2N aqueous sodium hydroxide solution for 30 minutes under reflux. The ethanol was then distilled off and the crude product was precipitated out by the addition of 2N hydrochloric acid. After recrystallization from ethanol, there was obtained 80 g. 3-chloro-6-nitrobiphenyl-4-carboxylic acid, which melted at 213° – 215°C.

100 g. ethyl 3-chloro-6-nitrobiphenyl-4-carboxylic acid were dissolved in 2.2 liters methanol and hydrogenated in the presence of Raney nickel. After filtering off the catalyst, the methanol was distilled off in a vacuum. As residue, there was obtained 87 g. 6-amino-3-chloro-biphenyl-4-carboxylic acid, which melted at 170° – 172°C.

86 g. 6-amino-3-chlorobiphenyl-4-carboxylic acid suspended in 430 ml. glacial acetic acid and 260 ml. concentrated hydrochloric acid and a solution of 24.9 g. sodium nitrite in 40 ml. water added thereto dropwise at 0° – 5°C. The diazotized mixture thus obtained was added to a solution of 650 g. sulfur dioxide in 860 ml. glacial acetic acid, which also contained 10 g. cupric chloride dihydrate, and the reaction mixture was stirred for 4 hours at ambient temperature. Thereafter, the reaction mixture was diluted with 4 liters ice water and the precipitated sulfochloride was filtered off with suction and introduced into 860 ml. concentrated aqueous ammonia solution. The reaction mixture was left to stand overnight, then treated with active charcoal and the crude product precipitated out by the addition of hydrochloric acid. After recrystallization thereof from ethanol, there was obtained 64 g. 3-chloro-6-sulfamoyl-biphenyl-4-carboxylic acid, which melted at 209° – 211°C.

The following compounds were obtained in an analogous manner:

3-thenylamino-6-sulfamoyl-biphenyl-4-carboxylic acid from 3-chloro-6-sulfamoyl-biphenyl-4-carboxylic acid and thenylamine; m.p. 214° – 216°C. (decomp.); yield 37% of theory; and 3-benzylamino-6-sulfamoyl-biphenyl-4-carboxylic acid from 3-chloro-6-sulfamoyl-biphenyl-4-carboxylic acid and benzylamine: m.p. 225° – 227°C. (decomp.); yield 53% of theory.

EXAMPLE 2

Preparation of
4-Tetrazolyl-(5)-3-thenylamino-6-sulfamoylbiphenyl 12 g. 3-chloro-4-cyano-6-sulfamoyl-biphenyl were heated to 80°C. for 6 hours with 35 ml. thenylamine. The reaction mixture was then poured into 2N hydrochloric acid and, after some time, the product which had become crystalline, was filtered off with suction, washed and dried. There was obtained 12 g. 4-cyano-3-thenylamine-6-sulfamoylbiphenyl which was heated to 80°C. for 8 hours with 2.2 g. sodium azide and 3.2 g. trimethyl ammonium chloride in 20 ml. dimethyl formamide. The reaction mixture was then diluted with 1N aqueous sodium hydroxide solution and extracted with ethyl acetate. The aqueous phase was acidified with 2N hydrochloric acid and the precipitated crude product was separated off. After recrystallization from ethanol, there was obtained 3.5 g. 4-tetrazolyl-(5)-3-thenylamino-6-sulfamoylbiphenyl, which melted at 238° – 240°C.

The 3-chloro-4-cyano-6-sulfamoyl-biphenyl used as starting material was prepared as follows:

25. g 3-chloro-6-sulfamoyl-biphenyl-4-carboxylic acid were boiled under reflux for 2 hours with 250 ml. thionyl chloride. Excess thionyl chloride was then distilled off in a vacuum and the residue was mixed, while cooling with ice, with 250 ml. concentrated aqueous ammonia solution. After an hour, the reaction mixture was concentrated somewhat and the precipitated crude product was filtered off with suction. After recrystallization from methanol, there was obtained 17 g. 3-chloro-6-sulfamoyl-biphenyl-4-carboxamide, which melted at 223° – 225°C.

15 g. 3-chloro-6-sulfamoyl-biphenyl-4-carboxamide were boiled under reflux for 1 hour with 150 ml. phosphorus oxychloride. After distilling off excess phosphorus oxychloride, the reaction mixture was carefully mixed with ice water. The precipitated crude product was separated off and recrystallized from methanol. There was obtained 12 g. 3-chloro-4-cyano-6-sulfamoylbiphenyl, which melted at 163° – 165°C.

EXAMPLE 3

Preparation of
3-Benzylamino-6-sulfamoyl-biphenyl-4-carboxylic acid

Variant I 1 g. 3-amino-6-sulfamoyl-biphenyl-4-carboxylic acid was dissolved in 10 ml. dimethyl formamide, 2 ml. benzyl chloride were added thereto and the reaction mixture was heated for 18 hours at 120°C. After cooling, the reaction mixture was mixed with 10 ml. water, rendered alkaline with a 2N aqueous solution of sodium carbonate and extracted with ether. The aqueous phase was treated with active charcoal, filtered and the filtrate acidified with 5N hydrochloric acid. The precipitated crude product was filtered off with suction and recrystallized from ethanol. There was obtained 0.50 g. (38% of theory) 3-benzylamino-6-sulfamoyl-biphenyl-4-carboxylic acid, which decomposed at 225° – 227°C.

The 3-amino-6-sulfamoyl-biphenyl-4-carboxylic acid used as starting material was prepared as follows:

A solution of 10 g. 3-chloro-6-sulfamoyl-biphenyl-4-carboxylic acid in 30 ml. methanol was heated for 14 hours at 130°C. in an autoclave with 90 ml. liquid ammonia. The reaction solution was then treated with active charcoal, filtered and the filtrate evaporated to dryness. The residue was taken up in 2N aqueous sodium hydroxide solution and extracted with methylene chloride. The aqueous phase was treated with active charcoal, filtered and the filtrate acidified with 2N hydrochloric acid. The crude product which separated out was taken up in ethyl acetate, washed with water, dried over anhydrous sodium sulfate and the solvent substantially distilled off in a vacuum. The oily residue was triturated with methylene chloride, whereupon it crystallized. The product was filtered off with suction, washed with methylene chloride and dried. There was obtained 4.8 g. (51% of theory) 3-amino-6-sulfamoyl-biphenyl-4-carboxylic acid, which decomposed at 223° – 224°C.

Variant II 0.2 g. platinum oxide in 50 ml. methanol were hydrogenated, a solution of 1 g. 3-amino-6-sulfamoyl-biphenyl-4-carboxylic acid and 1 ml. benzaldehyde in 20 ml. methanol were then added thereto and the reaction mixture was further hydrogenated. When no more hydrogen was taken up, the catalyst was filtered off and the filtrate was evaporated to dryness. The residue was taken up in 2N aqueous sodium carbonate solution and extracted with ethyl acetate. The aqueous phase was acidified with 5N hydrochloric acid and the precipitated crude product was filtered off with suction and recrystallized from ethanol. There was obtained 0.46 g. (35% of theory) 3-benzylamino-6-sulfamoylbiphenyl-4-carboxylic acid, which decomposed at 225° – 227°C.

The compounds of this invention possess outstanding saluretic properties as well. In order to establish the effectiveness of compounds representative of this invention as therapeutic agents for diuretic and saluretic purposes, the following series of tests were carried out.

The test animals were female Sprague-Dawley rats each weighing between 140°–200 grams. The rats were kept in climate controlled rooms at 23 ± 1°C and a relative humidity of 60 ± 5% for at least 1 week prior to the tests. On the evening prior to the test day (i.e., 16 hours prior to administration of test compounds), the test rats were left without food and had access only to drinking water. During the tests, groups of animals were placed into metabolic cages and such groups of animals were used in the tests. The test compounds were administered to the test animals as a suspension in 1% methyl cellulose at the rate of 10 milliliters per kg of body weight of each rat. The test preparations were administered orally. The dosage in terms of milligrams of test compounds per kg of body weight is set forth in the Table below. Prior to the test and after two hours and again after six hours subsequent to the test, the bladders of the rats were emptied by squeezing, the urine content was measured, sodium and potassium were determined by flame photometric tests, chlorine by titration.

The following were the test compounds:

Compound No.

| | |
|---|---|
| 1 | 3-Furfuryl-amino-6-sulfamoyl-biphenyl-4-carboxylic acid (invention) |
| A | FUROSEMID (= LASIX = 4-Chloro-(2-furylmethyl)-5-sulfamoyl-anthranilic acid) (prior art) |

Compound 1 is representative of the invention and a known compound, Compound A, was included for comparison purposes.

The results, which are set forth in Table 1 below, show that Compound 1 is markedly more effective in inducing excretion of urine and sodium and this effect was more pronounced after 6 hours than after 2 hours, indicating longer term effectiveness of the inventive compound.

In a second series of tests, dogs were used as the test animals and the measurements of effectiveness of the test compounds were made as before. The test animals were episiotomized beagles which were kept under fasting conditions, but with access to drinking water, for 16 hours prior to administration of the test compounds. The test compounds were administered to the test animals as a suspension in 1% methylcellulose at the rate of 1 milliliter per kg. of body weight of each dog.

The results of these tests are set forth in Table 2 below wherein $n$ (first column) stands for the number of test dogs used for each test substance. Again the test results show a greater effectiveness for Compound 1 relative to the prior art compound and again the effect was more marked after 6 hours than after 2 hours, indicating the longer persistent effect of the inventive compound.

the like, to which, if desired, can be added coloring and/or flavoring materials. Because of the low solubility of the new compounds according to the present invention, for injectable solutions only very few solvents can be considered, for example dimethyl sulfoxide. Consequently, higher concentrations are preferably administered in the form of suspensions. In human medicine, in the case of enteral administration, it has been found to be useful to administer between 10 and 500 mg. per day in 1 to 4 individual doses; in the case of intravenous administration, the most favorable amount of active materials is between 5 and 100 mg. per day.

The new compounds according to the present invention are characterized by a strong, rapidly-commencing diuretic action. Simultaneously with the increased excretion of water, an increased amount of sodium ions is also excreted. The simultaneously increased excretion of potassium ions which occurs in the case of the administration of comparable substances is substantially lower in the case of the new compounds according to the present invention. In this way, higher sodium-potassium quotients result, i.e., the new compounds according to the present invention permit a quickly, acutely and considerably increased excretion of water and of sodium ions without, at the same time, substantially impairing the potassium balance in the patients being treated.

It will be understood that the specification and examples are illustrative but not limitative of the present invention and that other embodiments within the spirit and scope of the invention will suggest themselves to those skilled in the art.

TABLE 1

Diuretic and Saluretic Properties of a Typical Compound of the Invention Relative to FUROSEMID (Urea and Salt Excretion in Rats*)

| Test Compound | Dosage mg/kg | ml urine | Two Hours Cl | Na | K | Separation/kg During Na K | ml urine | Six Hours Cl | Na | K | Na K |
|---|---|---|---|---|---|---|---|---|---|---|---|
| Control p.o. | — | 9 ±0.8 | 0.05 +0.008 | 0.10 +0.009 | 0.22 +0.012 | 0.5 | 13 ±1.0 | 0.39 ±0.042 | 0.43 ±0.037 | 0.62 ±0.035 | 0.7 |
| Compound A | 12 | 14 +1.0 | 0.97 ±0.111 | 0.57 ±0.098 | 0.42 ±0.030 | 1.4 | 17 ±1.1 | 1.4 ±0.16 | 0.88 ±0.149 | 0.74 ±0.101 | 1.2 |
| Compound 1 | 12 | 20 ±1.7 | 1.7 +0.21 | 1.3 ±0.19 | 0.40 +0.035 | 3.2 ±0.41 | 23 ±1.4 | 2.0 ±0.15 | 1.5 ±0.14 | 0.73 ±0.042 | 2.1 ±0.19 |

*Each test was based on results from six groups of five rats.

TABLE 2

Diuretic and Saluretic Properties of a Typical Compound of the Invention Relative to FUROSEMID (Urea and Salt Excretion in Dogs)

| n | Test Compound | Dosage mg/kg | ml urine | Two HOurs Cl | Na | K | Separation/kg During Na K | ml urine | Six Hours Cl | Na | K | Na K |
|---|---|---|---|---|---|---|---|---|---|---|---|---|
| 35 | Control p.o. | — | 1.7 ±0.21 | 0.04 ±0.01 | 0.09 ±0.02 | 0.14 ±0.02 | 0.6 | 4.6 +0.61 | 0.23 ±0.06 | 0.36 ±0.08 | 0.31 ±0.04 | 1.2 |
| 9 | Compound A | 2 | 17.6 ±2.4 | 2.4 ±0.33 | 2.1 ±0.34 | 0.46 ±0.06 | 4.6 | 22.7 ±2.3 | 2.8 ±0.31 | 2.5 ±0.35 | 0.71 ±0.09 | 3.5 |
| 12 | Compound 1 | 2 | 19.3 ±1.25 | 2.67 ±0.18 | 2.19 ±0.16 | 0.62 ±0.16 | 4.6 ±0.44 | 33.6 ±2.28 | 4.48 ±0.36 | 3.47 ±0.29 | 1.20 ±0.17 | 3.4 ±0.36 |

For the use of the new compounds according to the present invention as pharmaceuticals with a diuretic or natriuretic action, there can, in principle, be used all the conventional enteral and parenteral forms of administration. For this purpose, the active materials are admixed with solid or liquid pharmaceutical diluents or carriers and brought into a suitable form.

Examples of solid carrier materials include lactose, mannitol, starch, talc, methyl cellulose, gelatine and

What is claimed is:
1. Biphenyl compounds of the formula:

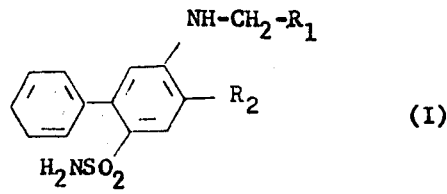

(I)

wherein
R$_1$ is furyl or thienyl; and
R$_2$ is carboxyl;
and the pharmacologically acceptable salts thereof.

2. Biphenyl compound as claimed in claim 1 wherein R$_1$ is furyl.

3. Biphenyl compound as claimed in claim 1 wherein R$_1$ is thienyl.

4. Biphenyl compound as claimed in claim 1 wherein R$_2$ is carboxyl.

5. Biphenyl compound as claimed in claim 1 wherein R$_1$ is furyl and R$_2$ is carboxyl.

6. Biphenyl compound as claimed in claim 1 wherein R$_1$ is thienyl and R$_2$ is carboxyl.

7. Biphenyl compound as claimed in claim 1 designated 3-furfurylamino-6-sulfamoyl-biphenyl-4-carboxylic acid.

* * * * *